(12) United States Patent
Bonde et al.

(10) Patent No.: US 10,201,702 B2
(45) Date of Patent: Feb. 12, 2019

(54) PELVIC FLOOR MUSCLE TRAINING

(75) Inventors: Eric H. Bonde, Minnetonka, MN (US); Xuan K. Wei, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1989 days.

(21) Appl. No.: 13/305,405

(22) Filed: Nov. 28, 2011

(65) Prior Publication Data

US 2012/0136413 A1 May 31, 2012

Related U.S. Application Data

(60) Provisional application No. 61/418,119, filed on Nov. 30, 2010.

(51) Int. Cl.
*A61N 1/36* (2006.01)
*A61N 1/372* (2006.01)

(52) U.S. Cl.
CPC ..... *A61N 1/36007* (2013.01); *A61N 1/36107* (2013.01); *A61N 1/36132* (2013.01); *A61N 1/37247* (2013.01)

(58) Field of Classification Search
CPC .......... A61N 1/36107; A61N 1/36007
USPC ....................................... 607/38–41
See application file for complete search history.

(56) References Cited

U.S. PATENT DOCUMENTS

| | | |
|---|---|---|
| 3,727,616 A | 4/1973 | Lenzkes |
| 3,870,051 A | 3/1975 | Brindley |
| 3,933,147 A | 1/1976 | Du Vall et al. |
| 4,102,344 A | 7/1978 | Conway et al. |
| 4,406,288 A | 9/1983 | Horwinski et al. |
| 4,515,167 A | 5/1985 | Hochman |
| 4,607,639 A | 8/1986 | Tanagho et al. |
| 4,612,934 A | 9/1986 | Borkan |
| 4,909,263 A * | 3/1990 | Norris ............................ 607/39 |
| 5,291,902 A | 3/1994 | Carman |
| 5,358,514 A | 10/1994 | Schulman et al. |
| 5,562,717 A | 10/1996 | Tippey et al. |
| 5,571,148 A | 11/1996 | Loeb et al. |
| 6,061,596 A | 5/2000 | Richmond et al. |
| 6,063,045 A | 5/2000 | Wax et al. |
| 6,721,603 B2 * | 4/2004 | Zabara et al. .................. 607/46 |
| 6,905,471 B2 | 6/2005 | Leivseth et al. |
| 7,387,603 B2 | 6/2008 | Gross et al. |

(Continued)

FOREIGN PATENT DOCUMENTS

WO 0137732 A1 5/2001

OTHER PUBLICATIONS

Treatment of Urge Incontinence with Combination Neuromodulation Techniques; Integrative Medicine; vol. 8, No. 1; Feb./Mar. 2009 to Earl A surwit, MD; Jill Campbell, RN, BSN; and Katny Karaszewski, RN< MBA, HCM.*

(Continued)

*Primary Examiner* — Paula J Stice

(74) *Attorney, Agent, or Firm* — Patterson Thuente Pedersen, P.A.

(57) ABSTRACT

Electrical stimulation is delivered to a patient based on input from a patient indicative of an intent of the patient to contract a pelvic floor muscle or an attempt by the patient to contract the pelvic floor muscle. The electrical stimulation is configured to induce a contraction of the pelvic floor muscle of the patient to strengthen the pelvic floor muscle.

32 Claims, 4 Drawing Sheets

(56) References Cited

U.S. PATENT DOCUMENTS

| 2004/0030360 | A1* | 2/2004 | Eini | A61B 5/04882 |
| | | | | 607/39 |
| 2006/0190046 | A9* | 8/2006 | Gerber | A61N 1/36071 |
| | | | | 607/39 |
| 2007/0027494 | A1* | 2/2007 | Gerber | 607/41 |
| 2009/0076565 | A1* | 3/2009 | Surwit | 607/41 |
| 2009/0138061 | A1 | 5/2009 | Stephens et al. | |

OTHER PUBLICATIONS

Treatment of Urge Incontinence with Combination Neuromodulation Techniques to Karaszewski et al published in Integrative Medicine, vol. 8, No. 1, Feb./Mar. 2009.*

* cited by examiner

PELVIC FLOOR MUSCLE TRAINING

This application claims the benefit of U.S. Provisional Application Ser. No. 61/418,119 by Bonde et al., which was filed on Nov. 30, 2010, and is entitled "PELVIC FLOOR MUSCLE TRAINING." U.S. Provisional Application Ser. No. 61/418,119 by Bonde et al. is incorporated herein by reference in its entirety

TECHNICAL FIELD

The disclosure relates to implantable medical devices and, more particularly, to delivering electrical stimulation using implantable medical devices.

BACKGROUND

Electrical stimulation systems may be used to deliver electrical stimulation therapy to patients to treat a variety of patient symptoms or conditions, such as pelvic floor disorders of patients. Pelvic floor disorders may include urinary incontinence (e.g., stress incontinence or urge incontinence), fecal incontinence, pelvic pain, bowel dysfunction, and sexual dysfunction. Some electrical stimulation systems include one or more electrodes coupled to an IMD via one or more leads, while other electrical stimulation systems include leadless stimulators.

SUMMARY

In general, the disclosure is directed to training a pelvic floor muscle of a patient with the aid of electrical stimulation. In some examples, a patient provides input (e.g., via a medical device programmer, an implantable medical device or another computing device) indicative of an intent to contract a pelvic floor muscle or an attempt to contract the pelvic floor muscle, and electrical stimulation is delivered to a nerve of the patient, e.g., a sacral nerve or a pudendal nerve of the patient or branches thereof, based on the input (e.g., in response to receiving the input). The electrical stimulation is configured to induce a contraction in the pelvic floor muscle to strengthen the pelvic floor muscle. In some examples, the systems and methods described herein may be used as part of a training program that can improve the patient's ability to control urination and/or defecation through strengthening of the pelvic floor muscles.

In one example, the disclosure is directed to a method that includes receiving input indicative of an intent of a patient to contract a pelvic floor muscle of the patient or an attempt by the patient to contract the pelvic floor muscle and delivering electrical stimulation to a nerve of the patient based on receiving the user input. The electrical stimulation is configured to induce a contraction of the pelvic floor muscle of the patient to strengthen the pelvic floor muscle.

In another example, the disclosure is directed to a system that includes at least one electrode implanted proximate to a nerve of a patient, an electrical stimulation module electrically coupled to the at least one electrode and configured to generate and deliver electrical stimulation, and a processor configured to receive input indicative of an intent of the patient to contract a pelvic floor muscle of the patient or an attempt by the patient to contract the pelvic floor muscle and to control the electrical stimulation generator to deliver electrical stimulation via the at least one electrode to the nerve of the patient based on receiving the user input. The electrical stimulation is configured to induce a contraction in the pelvic floor muscle of the patient to strengthen the pelvic floor muscle of the patient.

In another example, the disclosure is directed to a computer-readable medium comprising instructions that cause a processor to receive input indicative of an intent of a patient to contract a pelvic floor muscle of the patient or an attempt by the patient to contract the pelvic floor muscle and control an electrical stimulation module to deliver electrical stimulation to a nerve of the patient based on receiving the user input. The electrical stimulation is configured to induce a contraction of the pelvic floor muscle of the patient to strengthen the pelvic floor muscle. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory (RAM)) or any other type of volatile or non-volatile memory that stores instructions (e.g., in the form of a computer program or other executable) to cause a programmable processor to perform the techniques described herein.

In another example, the disclosure is directed to a system that includes means for receiving input indicative of an intent of a patient to contract a pelvic floor muscle of the patient or an attempt by the patient to contract the pelvic floor muscle and means for delivering electrical stimulation to a nerve of the patient based on receiving the user input. The electrical stimulation is configured to induce a contraction of the pelvic floor muscle of the patient to strengthen the pelvic floor muscle.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or RAM) or any other type of volatile or non-volatile memory that stores instructions (e.g., in the form of a computer program or other executable) to cause a programmable processor to perform the techniques described herein. The computer-readable medium may be nontransitory.

The details of one or more examples are set forth in the accompanying drawings and the description below. Other features, objects, and advantages will be apparent from the description and drawings, and from the claims.

DETAILED DESCRIPTION

Figure 1:
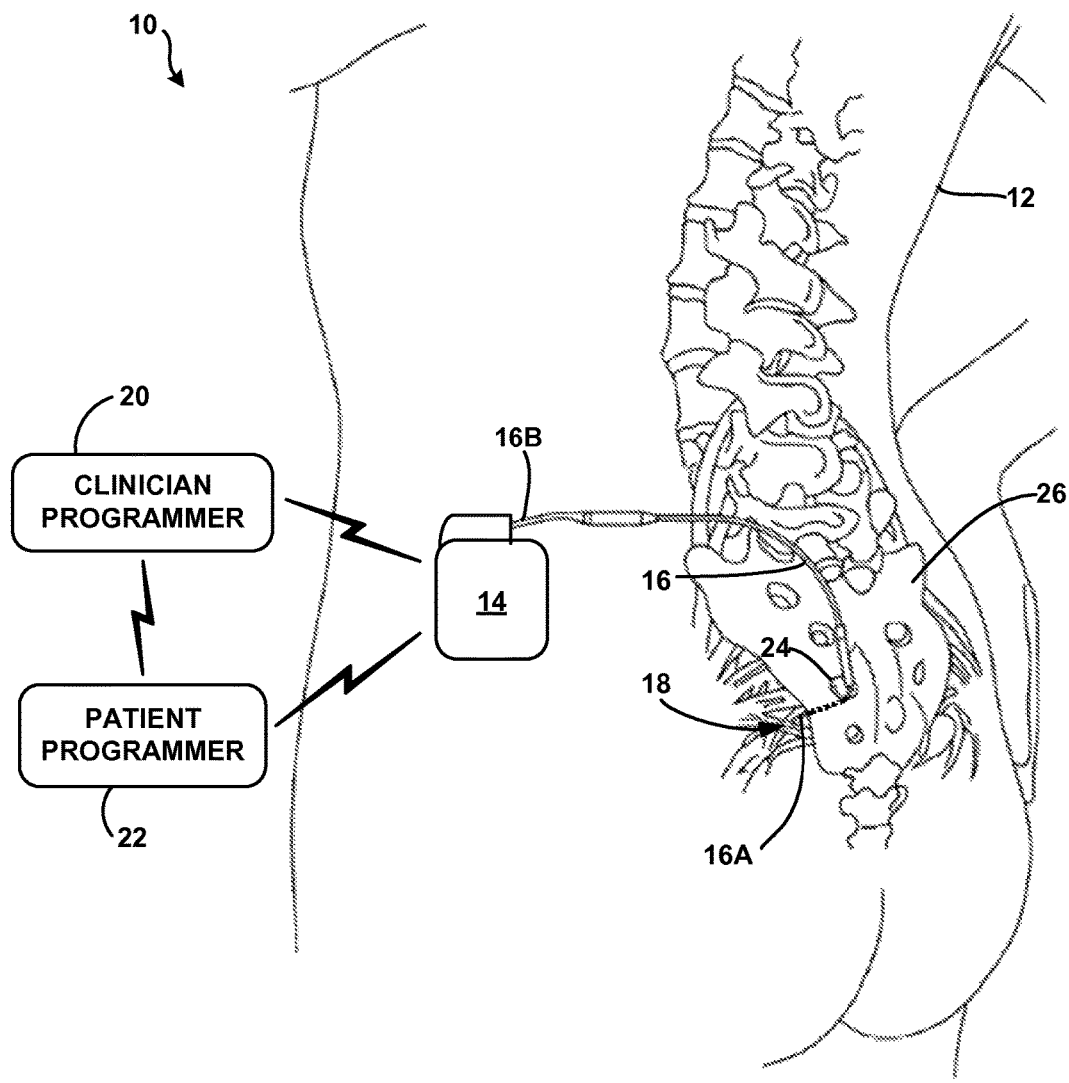
FIG. 1 is a schematic perspective view of an example implanted electrical stimulation system that includes an implantable medical device (IMD) coupled to a lead, a clinician programmer, and a patient programmer.

In some examples, pelvic floor disorders may result from weakening of one or more muscles in the pelvic region of the patient or, more specifically, from weakening of one or more pelvic floor muscles of a patient. The pelvic floor (which may also be referred to as the pelvic diaphragm) is generally composed of muscle fibers of the levator ani and the coccygeus, and associated connective tissue (e.g., collagen). The levator ani muscle is generally divided into the iliococcygeus muscle, the pubococcygeus muscle, and the puborectalis muscle. The pelvic floor muscles may also include sphincter muscles, such as the external urinary sphincter (EUS) and the external anal sphincter (EAS). Among other things, the pelvic floor provides support for organs of the pelvic region (e.g., the bladder, intestines, uterus, etc.), controls continence via the urinary and anal sphincters, controls sexual function, and, in female patients, plays a role in childbirth.

In some examples, one or more pelvic floor muscles of a patient may become weak or degenerated as a result of any number of conditions, e.g., injury, aging, pregnancy, and the like. Consequently, the patient may suffer from one or more pelvic floor disorders, such as urinary incontinence, fecal incontinence, or sexual dysfunction.

In some treatment regimens to manage pelvic floor disorders, patients may be instructed, e.g., by a clinician, to autonomously perform exercises for strengthening pelvic floor musculature in order to mitigate symptoms of the pelvic disorder. For example, in some examples, patients may be instructed to perform a regimen of Kegel exercises according to a schedule determined by a clinician. A Kegel exercise may refer to intentional contraction and relaxation of one or more pelvic floor muscles in order to strengthen the pelvic floor muscles. As an example, a traditional Kegel exercise may include stopping and restarting the flow of urine during urinary voiding in order to strengthen the external urethral muscles and the pubococcygeal muscles. In general, strengthening the patient's pelvic floor musculature may help to treat the patient's pelvic floor disorder. For example, in examples in which the patient suffers from urinary or fecal incontinence, strengthening the pelvic floor musculature may allow the patient to regain some or all control of voiding functions.

Although Kegel exercises may be effective for strengthening the pelvic floor muscles, some patients may be unable to properly perform the Kegel exercises. For example, in some examples, a patient may have difficulty identifying the proper muscles to contract. As another example, the patient may suffer from neural damage that prevents the patient from contracting the pelvic floor muscles, even if the patient is intent on contracting the proper muscles. As yet another example, the patient may have difficulty autonomously maintaining a regimen of Kegel exercises, e.g., the patient may forget to perform the Kegel exercises regularly. Consequently, in some of these examples, autonomous performance of Kegel exercises by the patient may not be sufficient or possible for strengthening the pelvic floor muscles.

The electrical stimulation systems and methods described herein are directed to delivering electrical stimulation to one or more nerves of a patient to induce contractions in the pelvic floor muscles to help strengthen the pelvic floor muscles of the patient. The systems may be described as neurostimulation systems in some examples. For example, in some examples, the electrical stimulation systems and methods described herein may electrically stimulate at least one nerve (e.g., to modulate activity of the nerve) to automatically induce contractions in the pelvic floor musculature similar to contractions that occur in properly-performed Kegel exercises. This type of electrical stimulation may be thought of as inducing an "electrical" or "automatic" Kegel exercise, and may partially or entirely eliminate the need for the patient to autonomously identify and contract the proper muscles to perform Kegel exercises.

In some examples, delivering electrical stimulation to a nerve to induce one or more contractions in pelvic floor musculature may provide one or more advantages in comparison to delivering stimulation directly to the muscle fibers of the pelvic floor musculature. For example, in some examples, delivering electrical stimulation to the nerve may require less energy, e.g., less intense stimulation and, consequently, less power, to induce a contraction in the muscle compared to delivering electrical stimulation directly to the muscle fibers of the muscle. In addition, delivering electrical stimulation to the nerve may induce a more coordinated contraction of the muscle than delivering electrical stimulation to the muscle fibers of the muscle. This may result in a more physiologically significant muscle contraction, which may better condition the patient's muscles for purposes of aiding in continence. Delivering electrical stimulation directly to the muscle fibers may require multiple electrical stimulation devices to induce contractions in each part of the muscle, which may be invasive and require sophisticated controls to achieve a coordinated contraction of the muscle. In contrast, delivering electrical stimulation to the nerve to induce the muscle contraction may require fewer, e.g., one, electrical stimulation devices to induce a coordinated contraction in a large portion of the muscle.

The patient may provide input to the electrical stimulation system that indicates that the patient is attempting to contract the pelvic floor muscles, and the input may initiate delivery of electrical stimulation by the electrical stimulation system to a target tissue site within the patient to induce the contraction in the pelvic floor muscles such that the patient intent to contract the pelvic floor muscles and the actual contraction of the muscles occurs substantially simultaneously. One or more electrodes may be implanted proximate to one or more target tissue sites, e.g., one or more nerves that influence the behavior of pelvic structures of the patient, such as the bladder, urinary sphincters, anal sphincters, and pelvic floor muscles. In some examples, the target tissue site may be a portion of a nerve of the patient, e.g., a sacral nerve, a pudendal nerve or a branch thereof, that can induce contraction in pelvic floor muscles of the patient. In other examples, the target tissue site may be a portion of tissue that is associated with the nerve such that, when electrical stimulation is delivered to the target tissue site, the nerve is stimulated. For example, the target tissue site may include tissue proximate to the nerve. In addition, in some examples, it may be desirable to stimulate a target tissue site that activates a proximal portion of the nerve, e.g., a portion of the nerve that is relatively close to the nerve trunk and/or to the central nervous system, such that the nerve activates a relatively large portion of muscle tissue. Some nerves combine and get larger (e.g., there may be more nerve fibers)

close to the central nervous system such that stimulation of a proximal portion of the nerve may induce contraction in more distal muscle tissue.

In some examples, repetitive delivery of electrical stimulation in this manner may allow the patient to regain control of his or her pelvic floor muscles over time and reduce the amount of treatment required to manage the patient's pelvic floor disorder. For example, repetitive delivery of electrical stimulation may establish new neural pathways within the patient's nervous system, in addition to or instead of strengthening the pelvic floor muscles. In some examples, the actual contraction of pelvic floor muscles may be neurologically re-wired to the intent or desire to contract the pelvic floor muscles. That is, the new neural connections may correlate the intention of the patient to contract the pelvic floor muscles to the actual contraction of the pelvic floor muscles, e.g., caused by the electrical stimulation delivery. Over time, the patient may gain or regain volitional control over the one or more pelvic floor muscles, such as the ability to autonomously contract the pelvic floor muscles simply by intending to contract the pelvic floor muscles, as a result of the new neural pathways. In examples in which the patient suffers from a voiding condition, e.g., urinary incontinence or fecal incontinence, this may allow the patient to regain autonomous control of his or her voiding functions over time, and may reduce or eliminate the need for electrical stimulation therapy to manage the voiding condition.

As another example, delivery of electrical stimulation in this manner in response to receiving patient input indicative of an intent to or attempt to contract one or more pelvic floor muscles may help tone and/or bulk the pelvic floor muscles, which may also help to promote the reflexes that promote continence. In this manner, the electrical stimulation systems and techniques described herein can be useful for addressing incontinence related to muscular deficiency and/or innervation deficiency.

FIG. 1 is a schematic perspective view of an electrical stimulation system 10 that is configured to provide therapy for a pelvic floor disorder of patient 12. Electrical stimulation system 10 receives input from a user, e.g., patient 12, indicating that patient 12 is attempting to contract one or more pelvic floor muscles, and delivers electrical stimulation to a target tissue site proximate a nerve of patient 12 based on the input. The electrical stimulation is configured to induce a contraction in the pelvic floor muscles in order to strengthen and train the pelvic floor muscles. The nerve can be a nerve that influences the behavior of pelvic floor muscles of patient 12, such as a sacral nerve, a pudendal nerve or a branch of the sacral or pudendal nerves. While the sacral and pudendal nerves are primarily referred to throughout the disclosure, in other examples, therapy system 10, as well as the other systems and methods for training and strengthening a pelvic floor nerve can include delivery of stimulation to tissue sites proximate other nerves in addition to or instead of the sacral or pudendal nerves. Moreover, reference to the sacral and pudendal nerves may include branches of the sacral and pudendal nerves that may also influence the behavior of pelvic floor muscles of patient 12.

Electrical stimulation system 10 includes implantable medical device (IMD) 14, which is coupled to lead 16, for delivering electrical stimulation to target tissue site 18 of patient 12. In addition, electrical stimulation system 10 includes clinician programmer 20 and patient programmer 22 for integrating a clinician and patient 12, respectively, into electrical stimulation system 10.

IMD 14 provides electrical stimulation therapy to target tissue site 18 located proximate a sacral nerve or a pudendal nerve of patient 12 by generating a programmable electrical stimulation signal (e.g., in the form of electrical pulses) and delivering the electrical stimulation signal to target tissue site 18 via lead 16. In some examples, lead 16 includes one or more stimulation electrodes, e.g., electrodes 40 (FIG. 2), disposed on distal end 16A of lead 16 and implanted proximate to target tissue site 18 such that the electrical stimulation is delivered from IMD 14 to target tissue site 18 via the stimulation electrodes.

In some examples described herein, target tissue site 18 includes at least one of a sacral nerve of patient 12 or a pudendal nerve of patient 12 (or a tissue site proximate the sacral or pudendal nerve, wherein delivery of electrical stimulation to the tissue site captures the nerve). The sacral and pudendal nerves of patient 12 may be involved in inducing a contraction in one or more muscles of the pelvic floor of patient 12. As a result, electrical stimulation of the sacral and/or pudendal nerves of patient 12 may be useful in treating the pelvic floor disorder of patient 12.

In general, the sacral nerves include five sacral nerves that emerge from the sacrum. In some examples, the sacral vertebrae (S1-S5) may be used to number the sacral nerves. The sacral nerves contribute to the sacral plexus (a network of intersecting nerves that innervates the posterior thigh, part of the lower leg, the foot, and part of the pelvis) and the coccygeal plexus (a network of intersecting nerves near the coccyx bone, e.g., the tailbone, that innervates the skin of the coccyx bone and around the anus). In general, the pudendal nerve is a somatic nerve in the pelvic region, which is a large branch of the sacral plexus. The pudendal nerve innervates the external genitalia, the urinary sphincters, and the anal sphincters.

As illustrated in FIG. 1, distal end 16A of lead 16 is implanted proximate to target tissue site 18. In the example shown in FIG. 1, target tissue site 18 is proximate the S3 sacral nerve of patient 12. In this example, in order to implant distal end 16A of lead 16 proximate to the S3 sacral nerve, lead 16 may be introduced into the S3 sacral foramen 24 of sacrum 26 to access the S3 sacral nerve. For some patients, stimulation of the S3 sacral nerve may be effective in treating a pelvic floor disorder of the patient. In other examples, distal end 16A may be implanted proximate to a different target tissue site, such as a target tissue site proximate to a different sacral nerve or a pudendal nerve of patient 12 to treat the pelvic floor disorder of patient 12.

In some examples, in order to confirm appropriate placement of electrodes of lead 16 proximate to the S3 sacral nerve, IMD 14 may deliver electrical stimulation via lead 16 and a clinician may look for signs of pelvic floor muscle contraction. For example, in some examples, if lead 16 is properly placed proximate to the S3 sacral nerve, delivery of stimulation via lead 16 may result in visible tightening of the levator ani muscles of patient 12 or a bellows response in the perineum or anal region of patient 12. In other examples, the clinician may look for other signs of pelvic floor muscle contraction.

Although FIG. 1 illustrates placement of lead 16 proximate to the S3 sacral nerve for delivery of stimulation to the S3 sacral nerve, in other examples, delivery of stimulation to the pudendal nerve of patient 12 may more specifically target the pelvic floor muscles of patient 12. For example, in some examples, stimulation of the S3 sacral nerve may activate one or more leg muscles of patient 12, in addition to activating one or more pelvic floor muscles. Activation of the one or more leg muscles may be unnecessary and unwanted in treatment for strengthening the pelvic floor muscles of patient 12. In some examples, stimulation of the pudendal nerve can more specifically target pelvic floor muscles, e.g., the external urethral sphincter, without activation of the one or more leg muscles.

Although FIG. 1 illustrates one lead 16, in some examples, IMD 14 may be coupled to two or more leads, e.g., to facilitate bilateral or multi-lateral stimulation. In some examples, lead 16 may also carry one or more sense electrodes via which IMD 14 can sense one or more physiological parameters (e.g., nerve signals, EMG, and the like) of patient 12, in addition to the one or more stimulation electrodes carried by lead 16. In some examples, lead 16 includes a lead body, and proximal end 16B of lead 16 may be electrically coupled to IMD 14 via one or more conductors extending substantially through the lead body between the one or more stimulation electrodes carried by lead 16 and IMD 14.

In the example shown in FIG. 1, lead 16 is cylindrical. One or more electrodes of lead 16 (e.g., electrodes 40 illustrated in FIG. 2) may be ring electrodes, segmented electrodes, or partial ring electrodes. Segmented and partial ring electrodes each extend along an arc less than 360 degrees (e.g., 90-120 degrees) around the outer perimeter of the lead 16. In some examples, segmented electrodes may be useful for targeting different fibers of the same or different nerves to generate different physiological effects or for delivering relatively high frequency stimulation (e.g., about 66 Hertz) and relatively low frequency stimulation (e.g., about 15 Hertz) to activate both fast twitch muscles and slow twitch muscles substantially simultaneously or at alternating time slots. In some examples, lead 16 may be, at least in part, paddle-shaped (i.e., a "paddle" lead).

In some examples, one or more of the electrodes of lead 16 may be cuff electrodes that are configured to extend at least partially around a nerve (e.g., extend axially around an outer surface of a nerve). In some cases, delivering stimulation via one or more cuff electrodes and/or segmented electrodes may help achieve a more uniform electrical field or activation field distribution relative to the nerve in some examples, which may help minimize discomfort to patient 12 that results from the delivery of electrical stimulation. An electrical field represents the areas of a patient anatomical region that are covered by an electrical field during delivery of electrical stimulation to tissue within patient 12. The electrical field may define the volume of tissue that is affected when the electrodes of lead 16 are activated. An activation field represents the neurons that will be activated by the electrical field in the neural tissue proximate to the activated electrodes.

The illustrated numbers and configurations of lead 16 and electrodes carried by lead 16 are merely one example. Different configurations, e.g., different quantities and/or positions of leads and electrodes, are possible. For example, in other examples, IMD 14 may be coupled to additional leads or lead segments having one or more electrodes positioned at different locations in the pelvic region of patient 12.

IMD 14 may be surgically implanted in patient 12 at any suitable location within patient 12, such as within in an abdomen of patient 12. In some examples, the implantation site may be a subcutaneous location in the side of the lower abdomen or the side of the lower back or upper buttocks. IMD 14 has a biocompatible outer housing, which may be formed from titanium, stainless steel, a liquid crystal polymer, or the like. In some examples, electrical conductors disposed within the lead body of lead 16 electrically connect electrodes, e.g., electrodes 40 (FIG. 2), to an electrical stimulation delivery module (e.g., electrical stimulation delivery module 28 of FIG. 2) within IMD 14. In other examples, therapy system 10 may include a leadless electrical stimulator, such as a microstimulator (e.g., a capsule shaped microstimulator), where the leadless electrical stimulator delivers electrical stimulation to target tissue site 18, and, in some examples, senses one or more physiological parameters of patient 12, via electrodes on an outer surface of the electrical stimulator housing and without the aid of electrodes of a lead that extends from the electrical stimulator housing.

Electrical stimulation system 10 receives input from patient 12, e.g., via patient programmer 22, indicating that patient 12 is attempting to contract one or more pelvic floor muscles or is intending on contracting the one or more pelvic floor muscles. The attempt to contract one or more pelvic floor muscles may or may not result in actual contraction of the muscle or a physiologically significant contraction of the muscle (e.g., a muscle contraction that affects physiological function, such as voiding, of patient 12). Based on receiving the input, such as in response to receiving the input, electrical stimulation system 10 controls delivery of electrical stimulation from IMD 14 to target tissue site 18, which is, e.g., a sacral nerve and/or a pudendal nerve of patient 12, via one or more electrodes of lead 16 (e.g., electrodes 40 of FIG. 2). In some examples, electrical stimulation system 10 receives the input and initiates delivery of electrical stimulation substantially simultaneously or substantially immediately (e.g., within 2 seconds or less, such as within one second or less) after receiving the patient input, which, in some examples, may result in formation of new neural pathways that, over time, may allow patient 12 to autonomously control his or her pelvic floor muscles. For example, in some examples, electrical stimulation system 10 delivers electrical stimulation as part of a training program or training schedule configured to strengthen the pelvic floor muscles over time. In this way, patient 12 may, in some examples, at least partially regain control over one or more functions controlled by the pelvic floor muscles. For example, patient 12 may regain control over urination and/or defecation functions, e.g., may be able to more effectively control urination or defecation, if the pelvic floor muscles of patient 12 are stronger.

In some examples, IMD 14 may deliver electrical stimulation other than the electrical stimulation for training or strengthening the pelvic floor muscles, and the electrical stimulation for training or strengthening the pelvic floor muscles may be activated secondarily. For example, in some examples, IMD 14 may be implanted to deliver electrical stimulation to manage a voiding disorder of patient 12 (e.g., functional electrical stimulation for urinary incontinence). In these examples, IMD 14 may deliver electrical stimulation configured to contract a muscle (e.g., the urinary sphincter) to help prevent involuntary voiding events in order to manage, e.g., urinary incontinence or fecal incontinence of patient 12. In addition or instead, IMD 14 may deliver electrical stimulation configured to relax a bladder of patient 12 to help prevent urgency.

In some examples, a clinician or caretaker of patient 12 may determine that patient 12 may benefit from training or strengthening of the pelvic floor muscles such that, over time, patient 12 may begin to control pelvic floor functions without the electrical stimulation delivered by IMD 14 or with less intense electrical stimulation therapy, e.g., in accordance with the systems and methods described herein. Consequently, in some examples, the clinician or caretaker may subsequently control IMD 14 to activate delivery of electrical stimulation as described herein in order to strengthen and train the pelvic floor muscles of patient 12. Using IMD 14 that is already implanted to deliver the electrical stimulation for strengthening and training the pelvic floor muscles may be advantageous because, for example, patient 12 may not require an additional implanted device for delivery of the electrical stimulation for strengthening and training the pelvic floor muscles, which may be convenient for patient 12.

In the example illustrated in FIG. 1, system 10 includes clinician programmer 20 and patient programmer 22. In some examples, one or both programmers 20 and 22 may be wearable communication devices integrated into a key fob or a wrist watch. In other examples, one or both programmers 20 and 22 may be handheld computing devices, computer workstations, or networked computing devices. Programmers 20 and 22 may include respective user interfaces that receive input from a user (e.g., a clinician or patient 12, respectively). The user interfaces may include components for interaction with a user, such as a keypad and a display. In some examples, the display may be a cathode ray tube (CRT) display, a liquid crystal display (LCD) or light emitting diode (LED) display and the keypad may take the form of an alphanumeric keypad or a reduced set of keys associated with particular functions. Programmers 20 and 22 can, additionally or alternatively, include a peripheral pointing device, e.g., a mouse, via which a user may interact with the user interface. In some examples, the displays may include a touch screen display, and a user may interact with programmers 20 and 22 via the touch screens of the displays. In some examples, the user may also interact with programmers 20 and 22 and/or IMD 14 remotely via a networked computing device.

Clinician programmer 20 facilitates interaction of a clinician with one or more components of system 10. In some examples, the clinician, (e.g., physician, technician, surgeon, electrophysiologist, or other clinician) may interact with clinician programmer 20 to communicate with IMD 14. For example, the clinician may retrieve physiological or diagnostic information from IMD 14 via clinician programmer 20. As another example, the clinician may interact with programmer 20 to program IMD 14, e.g., select values that define electrical stimulation generated and delivered by IMD 14, select other operational parameters of IMD 14, etc. As another example, the clinician may use programmer 20 to retrieve information from IMD 14 regarding the performance or integrity of IMD 14 or other components of system 10, such as lead 16 or a power source of IMD 14. In some examples, this information may be presented to the clinician as an alert if a system condition that may affect the efficacy of therapy is detected.

In some examples, a clinician may use clinician programmer 20 to create stimulation programs for electrical stimulation (generated and delivered by IMD 14) of the nerves configured to induce a contraction in pelvic floor muscles of the patient. In addition, in some examples, the clinician may use clinician programmer 20 to create one or more training schedules according to which one or more stimulation programs may be delivered to patient 12 in order to train the pelvic floor muscles of patient 12. The training schedules may, in some examples, specify the time duration of one or more stimulation programs, the number of times the electrical stimulation program is delivered within a particular period of time (e.g., daily), particular times of day at which the electrical stimulation program is delivered, and other parameters relating to the delivery of stimulation to patient 12 to train one or more pelvic floor muscles. In some examples, the clinician programmer 20 transmits the stimulation programs and/or the training schedules to IMD 14 for storage in a memory of IMD 14.

Patient programmer 22 facilitates interaction of patient 12 with one or more components of system 10. In some examples, patient 12 may interact with patient programmer 22 to control IMD 14 to deliver electrical stimulation, to manually abort the delivery of electrical stimulation by IMD 14, or to inhibit the delivery of electrical stimulation by IMD 14. Patient 12 may, for example, use a keypad or touch screen of programmer 22 to cause IMD 14 to deliver electrical stimulation, e.g., to activate one or more stimulation programs, to initiate one or more training schedules, and the like.

In some examples described herein, patient 12 may provide input to patient programmer 22 indicating that patient 12 is attempting to or intending on contracting one or more pelvic floor muscles. For example, in some examples, patient 12 may select a particular button of patient programmer 22 to indicate an intent or attempt of patient 12 to contract pelvic floor muscles or provide input to a touch screen of patient programmer 22 indicating intent or attempt of patient 12 to contract pelvic floor muscles. The button can be a dedicated button that is designated to receive input from patient 12 indicating an intent or attempt to contract pelvic floor muscles or the button can be a multifunction button, such as a soft key that changes function depending upon the section of the user interface currently viewed by patient 12 (or another user). After receiving the input, patient programmer 22 may transmit a signal to IMD 14 indicating that patient 12 is attempting to or intending on contract one or more pelvic floor muscles, and, in response to receiving the signal from programmer 22, IMD 14 may deliver electrical stimulation to a nerve of patient 12, e.g., a sacral or pudendal nerve or branches thereof, based on receiving the signal.

In other examples, one or more other components of therapy system 10 receives the patient input indicating an intent to or attempt to contract one or more pelvic floor muscles. For example, in some examples, patient 14 interacts with IMD 14 to provide the input. As an example, IMD 14 can include a motion sensor integrated into or on a housing of IMD 16, where the motion sensor is configured to generate a signal that is indicative of patient 12 tapping IMD 14 through the skin. The number, rate, or pattern of taps may be associated with the different types of input, such as input indicating an attempt to void and input indicating an intent to void. Patient 12 may provide the input by tapping IMD 14 and a processor of IMD 14 may identify the tapping of IMD 14 by patient 12 to determine when patient input is received and to control the delivery of stimulation that contracts the one or more pelvic floor muscles upon receiving the patient input.

Patient programmer 22 may also receive input from patient 12 related to a training schedule according to which IMD 14 delivers electrical stimulation to target tissue site 18. That is, in some examples, IMD 14 delivers the electrical stimulation to target tissue site 18 according to a training schedule, and patient 12 may provide input that defines one or more parameters of the schedule or initiates a training session during which IMD 14 delivers the electrical stimulation that causes one or more pelvic floor muscles of patient 12 to contract. For example, it may be desirable for IMD 14 to repetitively deliver electrical stimulation to target tissue site 18 in order to induce contractions that, over time, strengthen one or more pelvic floor muscles of patient 12. In addition, it may be desirable to balance the repetitiveness of the therapy with muscle recovery times in order to help prevent muscle fatigue from the stimulation. In some examples, IMD 14 delivers multiple sessions of electrical stimulation daily or over another period of time, multiple cycles of electrical stimulation per session. During each stimulation session, IMD 14 may generate and deliver stimulation according to predetermined therapy programs. In some examples, patient 12 may determine when the delivery of electrical stimulation may be convenient, e.g., not disruptive, not embarrassing, etc., for patient 12 and may provide input to patient programmer 22 to define the schedule of electrical stimulation delivery to accommodate these times, or provide input to patient programmer 22 that initiates the electrical stimulation delivery accordingly.

IMD 14, clinician programmer 20, and patient programmer 22 may communicate via wireless communication using any techniques known in the art. Examples of communication techniques may include, for example, low frequency or radiofrequency (RF) telemetry. Other techniques are also contemplated. In some examples, programmer 20 and/or programmer 22 may include a programming head that may be placed proximate to the patient's body near the IMD 14 implant site in order to improve the quality or security of communication between IMD 14 and programmers 20 and 22.

Figure 2:
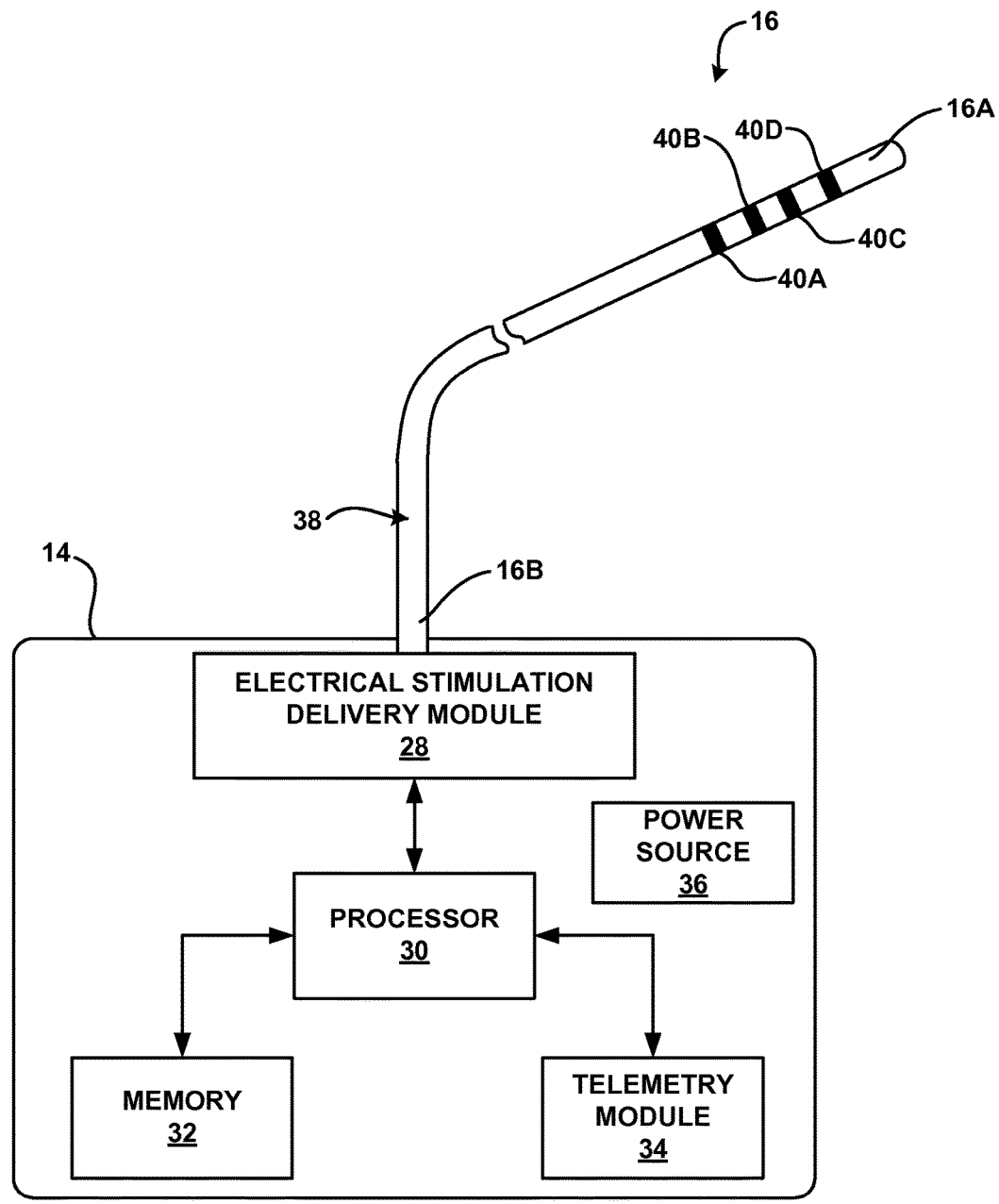
FIG. 2 is a block diagram illustrating components of an example IMD coupled to a lead.

FIG. 2 is a block diagram illustrating various components of an example IMD 14 and an example lead 16. In the example illustrated in FIG. 2, IMD 14 includes electrical stimulation module 28, processor 30, memory 32, telemetry module 34, and power source 36. In some examples, IMD 14 may also include a sensing module (not shown) and one or more sense electrodes for sensing a physiological parameter of patient 12, such as a muscle activity (e.g., via an electromyogram), neural activity or cardiac activity. Therapy system 10 can include other sensing modules in other examples, such as a motion sensor (e.g., an accelerometer, pressure transducer, gyroscope, or piezoelectric crystal) that generates a signal indicative of a patient posture state or patient activity level, a bladder volume sensor, or a sensor that generates a signal indicative of other voiding parameters of patient 12. The sensing module can be incorporated into IMD 14 or may be physically separate from IMD 14 and communicate with IMD 14 via a wired or wireless communication link. As illustrated in FIG. 2, lead 16 is electrically and mechanically coupled to IMD 14, and includes electrodes 40A-40D, which are configured to deliver electrical stimulation to target tissue site 18 (FIG. 1).

As discussed above, IMD 14 may deliver electrical stimulation to a sacral or pudendal nerve of patient 12 to induce a contraction in one or more pelvic floor muscles of patient 12 in order to strengthen the pelvic floor muscles of patient 12, and may control the delivery of the stimulation based on receiving input that patient 12 is intending to or attempting to contract the pelvic floor muscles. In some cases, over time, patient 12 may require less intense electrical stimulation because the pelvic floor muscles of patient 12 may be stronger as a result of the electrical stimulation, e.g., electrical stimulation simulating Kegel exercises, and patient 12 may gain or regain the ability to control contraction of the pelvic floor muscles, e.g., through new or improved neural connections formed as a result of the electrical stimulation regimen. Intensity of stimulation may be a function of various stimulation parameters, such as the amplitude, frequency, and/or signal duration of the stimulation signal and/or the electrodes with which IMD 14 delivers stimulation to target tissue site 18. In general, in order to strengthen the pelvic floor muscles, electrical stimulation module 28 generates and delivers electrical stimulation to target tissue site 18 under the control of processor 30. Processor 30 controls electrical stimulation module 28 to deliver electrical stimulation based on receiving input indicating that patient 12 is intending to or attempting to contract one or more pelvic floor muscles.

In some examples, telemetry module 34 receives, e.g., from patient programmer 22, an indication that patient 12 provided input indicating that patient 12 is attempting to or intending on contracting one or more pelvic floor muscles in anticipation of delivery of electrical stimulation by IMD 14. In some examples, the input may be provided by patient 12 via patient programmer 22, and transmitted to telemetry module 34 via a telemetry module of patient programmer 22. In other examples, the input may be provided by another user via another component of system 10, e.g., by a clinician via clinician programmer 20 or by patient 12 via interacting directly with IMD 14 (e.g., tapping the skin superior to the implanted IMD 14).

Processor 30 is configured to control electrical stimulation delivery module 28 to deliver electrical stimulation based on receiving input from patient 12, e.g., from patient programmer 22. For example, receipt of the input may be a trigger event that causes processor 30 to control electrical stimulation delivery module 28 to deliver electrical stimulation, such that the electrical stimulation is delivered in response to the input from patient 12. Telemetry module 34 includes any suitable hardware, firmware, software or any combination thereof for communicating with another device, such as clinician programmer 20 and/or patient programmer 22 (FIG. 1). Under the control of processor 30, telemetry module 34 may receive downlink telemetry, e.g., patient input, from and send uplink telemetry, e.g., an alert, to another device with the aid of an antenna, which may be internal and/or external. Processor 30 may provide the data to be uplinked to another device and the control signals for the telemetry circuit within telemetry module 34, and receive data from telemetry module 34.

In some examples, electrical stimulation module 28 delivers electrical stimulation for a predetermined period of time, where the initiation of the stimulation is controlled by patient 12. In some of these examples, the stimulation delivery does not coincide with the contraction of one or more pelvic floor muscles by patient 12, whereas in other examples, the stimulation delivery coincides with the contraction of the one or more pelvic floor muscles by patient 12. In some examples, patient 12 interacts with patient programmer 22 to control the delivery time, e.g., to initiate the delivery of the stimulation. In operation, processor 30 may receive the patient input via telemetry module 34 and control electrical stimulation module 28 to deliver therapy according to the received input. In other examples, patient 12 may interact with IMD 14 to control the delivery time, and processor 30 may receive the input from patient 12 (e.g., by detecting a particular pattern of tapping of IMD 14) and control electrical stimulation module 28 to deliver therapy according to the received input.

In some examples, upon receiving input from patient 12 indicating that patient 12 is attempting to contract one or more pelvic floor muscles or is intending on contracting one or more pelvic floor muscles, processor 30 controls electrical stimulation module 28 to generate and deliver electrical stimulation according to one or more electrical stimulation programs stored in memory 32. That is, in some examples, memory 32 may store one or more electrical stimulation programs and processor 30 may access the programs and control electrical stimulation delivery module 28 to generate and deliver electrical stimulation according to a selected one or more of the programs. Consistent with the techniques described in this disclosure, in some examples, processor 30 may load one or more stimulation programs stored in memory 32 to electrical stimulation module 28 based on input received from patient 12, which may be received by IMD 14 or may be transmitted to IMD 14 via telemetry module 34, e.g., via patient programmer 22.

Electrical stimulation module 28 delivers electrical stimulation according to particular stimulation parameters, such as voltage or current amplitude, frequency (e.g., pulse rate in the case of stimulation pulses), and signal duration (e.g., pulse width in the case of stimulation pulses). The stimulation parameters can also include one or more electrodes 40 with which electrical stimulation module 28 delivers stimulation to patient 12. In some examples, the stimulation parameters may be specified by one or more stimulation programs, e.g., one or more stimulation programs stored within memory 32. In some examples, electrical stimulation module 28 delivers therapy in the form of electrical pulses. In other examples, electrical stimulation delivery module 28 delivers electrical stimulation in the form of continuous waveforms.

In some examples, the stimulation parameters defining the electrical stimulation delivered to target tissue site 18 are selected to induce a contraction in one or more pelvic floor muscles of patient 12. For example, with the aid of clinician programmer 20, a clinician may select the stimulation parameter values that induce a contraction of the one or more pelvic floor muscles of patient 12. The specific pelvic floor muscles of patient 12 may depend upon the type of pelvic floor disorder that afflicts patient 12. In some examples, the stimulation parameters may be selected to activate particular types of tissue within patient 12.

As an example, in some examples, it may be desirable to activate a particular type of muscle fiber in the pelvic floor muscles of patient 12, e.g., fast-twitch muscle fibers, medium-twitch muscle fibers, or slow-twitch muscle fibers. Stimulation defined by particular stimulation parameter values and delivered to a sacral or pudendal nerve of patient 12 may activate various types of pelvic floor muscle fibers. Fast twitch muscle fibers include muscle fibers that contract quickly and powerfully but may fatigue very rapidly. In contrast, slow twitch muscle fibers include muscle fibers that contract for long periods of time but with a smaller force than the fast twitch muscles. In some examples, fast twitch pelvic floor muscle fibers and slow twitch pelvic floor muscle fibers may have substantially different functions. For example, in some examples, with respect to urinary disorders, fast twitch muscle fibers may be at least partially responsible for initiating closure of the urinary sphincter and the periurethral muscles (e.g., the muscles surrounding the urethra) and slow twitch muscle fibers may be at least partially responsible for maintaining closure of the urinary sphincter and the periurethral muscles. Consequently, depending upon the application, in some examples, the particular stimulation parameters may be selected to activate one or a combination of fast twitch or slow twitch pelvic floor muscle fibers.

In some examples, memory 32 stores one or more stimulation programs that each defines at least one set of stimulation parameter values configured to activate different pelvic floor muscle fibers or different combinations of pelvic floor muscle fibers. For example, memory 32 can store one set of stimulation parameter values configured to activate fast-twitch muscle fibers in order to maximize closure of the urinary sphincter and/or periurethral muscles, and another set of stimulation parameter values that are configured to activate slow-twitch muscle fibers in order to maintain closure of the urinary sphincter and/or periurethral muscles while minimizing muscle fatigue. The fast-twitch and slow-twitch muscle fibers may be selectively activated by activating specific nerve fibers with the same electrodes of a common lead, or different electrodes of a common lead (e.g., segmented electrodes specifically selected to target particular nerve fibers) or electrodes of separate leads or leadless electrical stimulators (e.g., microstimulators). In some examples, memory 32 can also store a third set of stimulation parameter values that is configured to activate both the slow-twitch and fast-twitch muscle fibers.

In general, electrical stimulation module 28 generates and delivers electrical stimulation defined by particular parameters, e.g., particular amplitude values, frequency values, electrode combinations, etc. In some examples, electrical stimulation module 28 generates and delivers stimulation to patient 12 that is configured to induce a contraction of one or more pelvic floor muscles in response to receiving patient input that indicates, e.g., patient 12 is attempting to contract the one or more pelvic floor muscles or is intending on attempting to contract the muscles within a particular time range (e.g., within the next minute or less, such as within the few seconds following the patient input).

In addition to or instead of the stimulation delivered in response to the patient input, in some examples, electrical stimulation module 28 generates and delivers electrical stimulation according to a particular training schedule configured to strengthen and train one or more pelvic floor muscles of patient 12. In some examples, the schedule may specify delivery of only one stimulation session while, in other examples, the schedule may specify delivery of multiple stimulation sessions at particular points in time. For example, the schedule may specify the number of stimulation sessions (e.g., one, two or more) within a 24 hour period of time, as well as the timing of the stimulation sessions relative to each other and/or relative to the time of day.

In some examples, the training schedule may specify the number of cycles of electrical stimulation within a given stimulation session. One cycle of electrical stimulation may be defined by an "on period" in which stimulation (e.g., continuous stimulation or pulses of stimulation) is delivered and an "off period" in which no stimulation is delivered. Each stimulation session may include a plurality of cycles of electrical stimulation in some examples.

The training schedule may also specify the time duration of on periods and off periods in each cycle. In addition, the training schedule may specify the time duration of one or more stimulation sessions, the number of stimulation sessions to be delivered, and, if pertinent, the schedule with which the stimulation sessions are initiated. The schedule can be a function of, for example, the amount of time between stimulation sessions, the particular point in time at which stimulation is to be delivered, a number of repetitions of a stimulation session of a particular period of time (e.g., daily), and similar such temporal parameters. In some examples, the electrical stimulation parameter values and/or the training schedule may be stored in memory 32, and processor 30 may access the information in order to control electrical stimulation module 28 to deliver electrical stimulation.

As an example, in some examples, processor 30 controls electrical stimulation module 28 to generate and deliver stimulation pulses having a frequency of between approximately 20 Hz and approximately 50 Hz in order to activate a combination of slow twitch, medium twitch, and fast twitch pelvic floor muscle fibers. In some examples, electrical stimulation delivery module 28 delivers the electrical stimulation according to a training schedule that defines one or more stimulation sessions, each of which may be characterized by an on period of approximately ten seconds followed by an off period of approximately twenty seconds. The training schedule may specify a time duration of each stimulation session (e.g., approximately 20 minutes), and processor 30 may control electrical stimulation delivery module 28 to deliver two stimulation sessions daily for a limited period of time (e.g., a week or month) or for an indefinite amount of time (until otherwise stopped by a clinician or patient 12).

As another example, processor 30 may control electrical stimulation module 28 to generate and deliver stimulation pulses having a relatively high frequency (e.g., between approximately 50 Hz and approximately 70 Hz, e.g., approximately 66 Hz) to activate fast-twitch muscle fibers. In some examples, the stimulation program to activate fast-twitch muscle fibers may be characterized by a training schedule specifying one or more stimulation sessions, each of which includes an on period of approximately three seconds followed by an off period of approximately 40 seconds. As another example, processor 30 may control electrical stimulation delivery module 28 to generate and deliver stimulation pulses at a lower relative frequency (e.g., between approximately 10 Hz and approximately 30 Hz) to activate slow-twitch muscle fibers. In some examples, the stimulation program to activate slow-twitch muscle fibers may be characterized by a training schedule specifying one or more stimulation sessions, each of which includes an on period of approximately five seconds, followed by an off period of approximately 40 seconds in which electrical stimulation is not delivered. Delivery of electrical stimulation in this manner may minimize fatigue of fast twitch muscle fibers and slow twitch muscle fibers (e.g., by providing sufficient time for the muscle fibers to recover from contraction) while also providing a large contraction force in each stimulation session, which can result in increased strengthening of the pelvic floor muscle fibers.

In some examples, electrical stimulation module 28 generates and delivers stimulation pulses that are configured to activate a first type of muscle fiber for a first period of time and subsequently generates and delivers stimulation pulses that are configured to activate a second type of muscle fiber for a second period of time. The second period of time may immediately follow the first period or time, or may be spaced from the first period of time by a predetermined amount of time (e.g., one second to about 5 minutes or more) For example, in some examples, a training schedule may specify that electrical stimulation module 28 delivers stimulation configured to activate fast twitch muscle fibers for approximately one minute and subsequently delivers stimulation configured to activate slow twitch muscle fibers for approximately twenty minutes. Alternatively or additionally, the training schedule may specify that electrical stimulation module 28 repeats this regimen approximately every 2 hours during the day, e.g., between approximately 8:00 AM and approximately 8:00 PM or during the patient's awake hours as determined, e.g., based on one or more patient parameters that are indicative of a sleep or awake state of patient 12.

As another example, a training schedule may specify that electrical stimulation delivery module 28 delivers stimulation configured to activate fast twitch muscle fibers for approximately 10 minutes immediately followed by stimulation configured to activate slow twitch muscle fibers for approximately 20 minutes. The training schedule may also specify one minute of rest per five induced muscle contractions in two sessions daily. Other training schedules are contemplated and can be configured to be specific to patient 12 or to be more general and applied to patient 12.

In some examples, the portion of the electrical stimulation that activates the fast twitch muscle fibers may be delivered for a shorter duration of time than the portion of the second stimulation therapy that activates the slow twitch muscle fibers. This may help minimize muscle fatigue by providing the fast twitch muscle fibers with a longer recovery time. It has been found that some fast twitch muscle fibers require a longer time to recover, e.g., to regain contraction force, following the delivery of stimulation, in comparison to slow twitch muscle fibers. Muscles may be recovered when the contraction force under stimulation is close or substantially equal to the contraction force under the same stimulation intensity while there is no fatigue e.g., when the muscles are stimulated a first time after a relatively long time of rest in which no stimulation was delivered. If the muscle is stimulated again with the same therapy parameter values, and the contraction force is the same, then the muscle may be considered to have recovered from the previous delivery of stimulation.

An example range of stimulation parameters for electrical stimulation that are likely to be effective in inducing a contraction of one or more pelvic floor muscles when applied to the sacral or pudendal nerves are as follows:

1. Frequency: between approximately 0.5 Hz and approximately 500 Hz, such as between approximately 10 Hz and approximately 250 Hz, or between approximately 20 Hz and approximately 60 Hz, such as about 40 Hz.

2. Amplitude: between approximately 0.1 volts and approximately 50 volts, such as between approximately 0.5 volts and approximately 20 volts, or between approximately 1 volt and approximately 10 volts.

3. Pulse Width: between approximately 10 microseconds (μs) and approximately 5000 μs, such as between approximately 50 μs and approximately 1000 μs, or between approximately 120 μs and approximately 450 μs.

As discussed, memory 32, another component of system 10 (e.g., one or both programmers 20, 22) or an external storage device (e.g., a remote database in communication with at least one programmer 20, 22 and/or IMD 14) may store one or more training schedules for delivery of electrical stimulation. In some examples, processor 30 can automatically activate the one or more training schedules, e.g., at a particular time of day. In some examples, the training schedule may be displayed to patient 12, e.g., via patient programmer 22, such that patient 12 can provide input regarding the training schedule. For example, in some examples, patient 12 can provide input that defines a training schedule (e.g., input defining the start times for each of the stimulation sessions) that is convenient for patient 12. In other examples, patient 12 may override an automatically implemented training program, e.g., if the training program may be disruptive or embarrassing for patient 12. Moreover, in some examples, prior to activation of a training schedule, IMD 14 or another component (e.g., one or both programmers 20, 22) can generate a notification to inform patient 12 that the training program will be automatically activated, and, in some cases, patient 12 is given the opportunity to abort the training session, such as by providing input to patient programmer 22 or by directly interacting with IMD 14 (e.g., by tapping the skin superior to the implanted IMD 14). The notification can be a visual notification, an audible notification, a somatosensory notification (e.g., a vibration of a housing of IMD 14 or the respective programmer 20, 22), or any combination thereof.

In some examples, IMD 14 may deliver electrical stimulation to induce contraction of the one or more pelvic floor muscles during a voiding event, which may help patient 12 or a clinician to determine whether the electrical stimulation is properly configured to exercise the pelvic floor musculature of patient 12 or to confirm the proper muscles are being contracted by the stimulation. For example, in some examples, a proper contraction of the pelvic floor musculature may induce closure of the external urinary sphincter (EUS) of patient 12, which stops the flow of urine during a urinary voiding event. Consequently, if the electrical stimulation is properly configured to induce contraction of the pelvic floor muscles, delivering the electrical stimulation during a urinary voiding event results in stoppage of the flow of urine, which may indicate to patient 12 or the clinician that the electrical stimulation is properly configured. Similarly, as another example, IMD 14 may deliver electrical stimulation during a defecation voiding event to confirm closure of the external anal sphincter (EAS), e.g., as evidenced by stoppage of defecation, to determine that the electrical stimulation is properly configured to induce contraction of the pelvic floor muscles.

In the example of FIG. 2, electrical stimulation module 28 drives a single lead 16. Specifically, electrical stimulation module 28 delivers electrical stimulation to tissue of patient 12 via selected electrodes 40A-40D carried by lead 16. Proximal end 16B of lead 16 extends from the housing of IMD 14 (e.g., directly or indirectly via one or more lead extensions) and distal end 16A of lead 16 extends to target therapy site 18, which can include one or more tissue sites proximate to a sacral nerve or a pudendal nerve, or both sacral and pudendal nerves. In other examples, electrical stimulation module 28 delivers electrical stimulation with electrodes on more than one lead and each of the leads may carry one or more electrodes. The leads may be configured as an axial lead with ring, partial ring or segmented, electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 14. In yet other examples, processor 30 may act as a "master" module that controls one or more microstimulators to deliver stimulation at target tissue sites.

Lead body 38 of lead 16 may have any suitable configuration. For example, in some examples, lead body 38 is cylindrical, as illustrated in FIG. 2. In other examples, lead body 38 may have another configuration, such as a paddle-shaped lead body (e.g., lead 16 may be a paddle lead). In the example illustrated in FIG. 2, lead body 38 defines the longitudinal outer surface of lead 16, which is generally the surface extending between distal end 16A and proximal end 16B of lead 16. In other examples, such as examples in which lead body 18 is non-cylindrical, the longitudinal outer surface may be generally referred to as the longest dimension of the lead body 38. In the example illustrated in FIG. 2, electrodes 40A, 40B, 40C, and 40D (collectively "electrodes 40") are disposed on lead body 38 adjacent to distal end 16A of lead 16. Electrodes 40 may be electrically coupled to electrical stimulation module 28 of IMD 14 via one or more conductors extending through lead body 38, such that electrical stimulation delivery module 28 can generate and deliver electrical stimulation to target tissue site 18 via one or more of electrodes 40.

Electrodes 40 may be any electrodes suitable for delivering electrical stimulation to target tissue site 18. The configuration, type, and number of electrodes 40 illustrated in FIG. 2 are merely one example, and, in other examples, lead 16 can include any suitable number of electrodes in any suitable configuration. In addition, in some examples, electrodes 40 may also include one or more sense electrodes that sense one or more physiological parameters of patient 12. In the example illustrated in FIG. 2, electrodes 40 are ring electrodes. In other examples, electrodes 40 may be segmented or partial ring electrodes. In examples in which lead 16 is a paddle lead, electrodes 40 may extend along a portion of the periphery defined by lead body 38. Electrodes 40 extending around a portion of the circumference of lead body 38 (e.g., around less than approximately 360 degrees of the circumference of lead body 38) or along one side of a paddle lead may be useful for providing electrical stimulation in a particular direction and/or for targeting a particular target tissue site, e.g., target tissue site 18. For example, in some examples, electrodes 40 may be disposed along lead body 38 such that one or more of electrodes 40 face toward particular target tissue sites, e.g., particular nerves. In some examples, such a configuration of electrodes 40 may facilitate more efficient delivery of electrical stimulation, in comparison to electrical stimulation delivered via one or more ring electrodes 40, because stimulation of tissue surrounding the target tissue site may not be necessary.

Processor 30 is configured to control telemetry module 34 to exchange information with clinician programmer 20 and/or patient programmer 22. Processor 30 may transmit operational information and receive stimulation programs or stimulation parameter adjustments via telemetry module 34. Also, in some examples, IMD 14 may communicate with other implanted devices, such as stimulators, control devices, or sensors, via telemetry module 34.

The processors described in this disclosure, such as processor 30, may be one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Memory 32 may also store instructions for execution by processor 30. Memory 32 may include separate memories for storing instructions, electrical signal information, stimulation programs, etc. Memory 32 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 32 may store program instructions that, when executed by processor 30, cause IMD 14 to perform the functions ascribed to IMD 14 herein.

Power source 36 is configured to deliver operating power to the components of IMD 14. Power source 36 may include a battery and a power generation circuit to produce the operating power. In some examples, the battery may be rechargeable to allow extended operation. Recharging may be accomplished through proximal inductive interaction between an external charger and an inductive charging coil within IMD 14. In other examples, an external inductive power supply may transcutaneously power IMD 14 whenever stimulation therapy is to occur.

Figure 3:
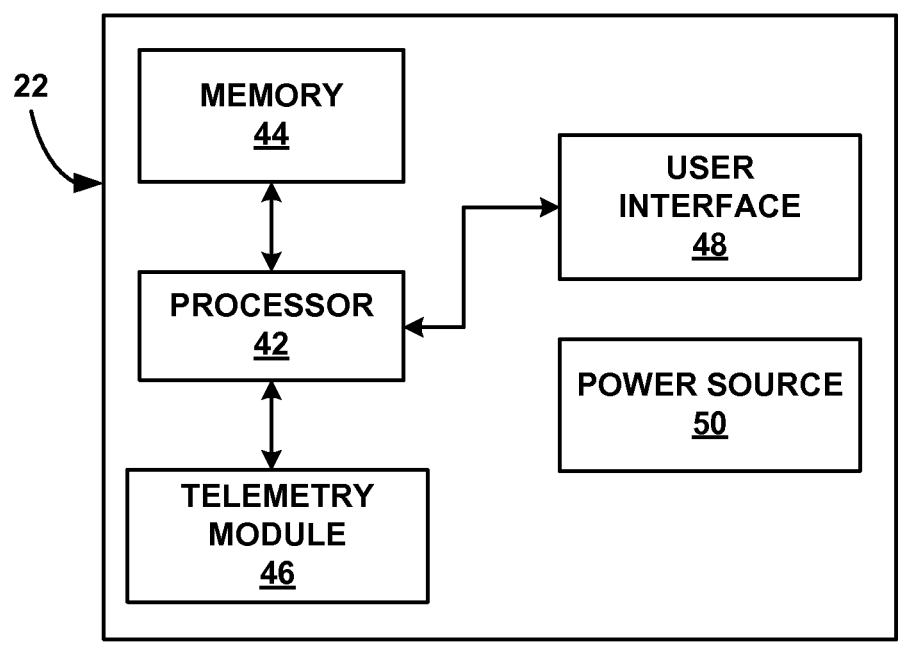
FIG. 3 is a functional block diagram illustrating components of an example medical device programmer.

FIG. 3 is a block diagram illustrating example components of patient programmer 22 (FIG. 1). While patient programmer 22 may generally be described herein as a hand-held computing device, in other examples, patient programmer 22 may be a notebook computer, a cell phone, or a workstation, for example. As illustrated in FIG. 3, patient programmer 22 may include a processor 42, memory 44, telemetry module 46, user interface 48, and power source 50. Memory 44 may store program instructions that, when executed by processor 42, cause processor 42 and patient programmer 22 to provide the functionality ascribed to patient programmer 22 throughout this disclosure.

In some examples, memory 44 may further include program information, e.g., stimulation programs similar to those stored in memory 32 of IMD 14. In some examples, the stimulation programs stored in memory 44 may be downloaded into memory 32 of IMD 14. Memory 44 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processor 42 can take the form one or more microprocessors, DSPs, ASICs, FPGAs, programmable logic circuitry, or the like, and the functions attributed to processor 42 herein may be embodied as hardware, firmware, software or any combination thereof.

User interface 48 is configured to receive input from a user and may include, for example, a button or keypad, lights, a speaker for voice commands, a display, such as a LCD, LED, or CRT. In some examples the display may be a touch screen. In some examples, processor 42 may receive patient input, e.g., patient input indicating that patient 12 is intending to or attempting to contract one or more pelvic floor muscles, via user interface 48. The input may be, for example, in the form of pressing a button on a keypad or selecting an icon from a touch screen. In response to receiving the input, processor 42 may, for example, control telemetry module 46 to deliver a signal that indicates receipt of the input to IMD 14, clinician programmer 20 or another device. This signal may, for example, cause the delivery of electrical stimulation to patient 12.

Processor 42 may also be configured to present information, e.g., information related to one or more sessions of electrical stimulation, electrical stimulation parameters, schedules of delivery of electrical stimulation, initiation of a particular stimulation session, and the like, to patient 12 or another user (e.g., a patient caretaker) via user interface 48. Although not shown, patient programmer 22 may additionally or alternatively include a data or network interface to another computing device, to facilitate communication with another device, e.g., IMD 14, and presentation of information relating to electrical stimulation via the other device.

Telemetry module 46 supports wireless communication between IMD 14 and patient programmer 22 under the control of processor 42. Telemetry module 46 may also be configured to communicate with another computing device, such as clinician programmer 20, via wireless communication techniques, or direct communication through a wired connection. Telemetry module 46 may be substantially similar to telemetry module 34 described above, providing wireless communication via an RF or proximal inductive medium. In some examples, telemetry module 46 may include an antenna, which may take on a variety of forms, such as an internal or external antenna. An external antenna that is coupled to patient programmer 22 may correspond to a programming head that may be placed over IMD 16.

Examples of local wireless communication techniques that may be employed to facilitate communication between patient programmer 22 and another computing device include RF communication according to the 802.11 or Bluetooth specification sets, infrared communication, e.g., according to the IrDA standard, or other standard or proprietary telemetry protocols. In this manner, other external devices may be capable of communicating with patient programmer 22 without needing to establish a secure wireless connection.

IMD 14 and/or patient programmer 22 may control the delivery of electrical stimulation according to one or more stimulation programs based on input indicating an attempt by or an intent of patient 12 to contract one or more pelvic floor muscles. In some examples in which patient programmer 22 controls the stimulation, patient programmer 22 may transmit stimulation programs (e.g., the actual parameter values or an indication of the stimulation program) for implementation by IMD 14 to IMD 14 via telemetry module 46. In some examples, a user (e.g., patient 12 or a clinician) may select one or more stimulation programs from a list provided via a display of user interface 48. Alternatively, patient programmer 22 may transmit a signal to IMD 14 indicating that IMD 14 should execute locally stored programs or therapy schedules. In such a manner, control over the electrical stimulation may be distributed between IMD 14 and patient programmer 22, or may reside in either one alone.

Power source 50 is configured to deliver operating power to the components of patient programmer 22. Power source 50 may include a battery and a power generation circuit to produce the operating power. In some examples, the battery may be rechargeable to allow extended operation. Recharging may be accomplished by electrically coupling power source 50 to a cradle or plug that is connected to an alternating current (AC) outlet. Additionally or alternatively, recharging may be accomplished through proximal inductive interaction between an external charger and an inductive charging coil within patient programmer 22. In other examples, traditional batteries (e.g., nickel cadmium or lithium ion batteries) may be used. In addition, patient programmer 22 may be directly coupled to an alternating current outlet to power patient programmer 22. Power source 50 may include circuitry to monitor power remaining within a battery. In this manner, user interface 48 may provide a current battery level indicator or low battery level indicator when the battery needs to be replaced or recharged. In some cases, power source 50 may be capable of estimating the remaining time of operation using the current battery.

In some examples, clinician programmer 20 includes components similar to those of patient programmer 22 shown in FIG. 3. However, other configurations of clinician programmer 20 are contemplated.

Figure 4:
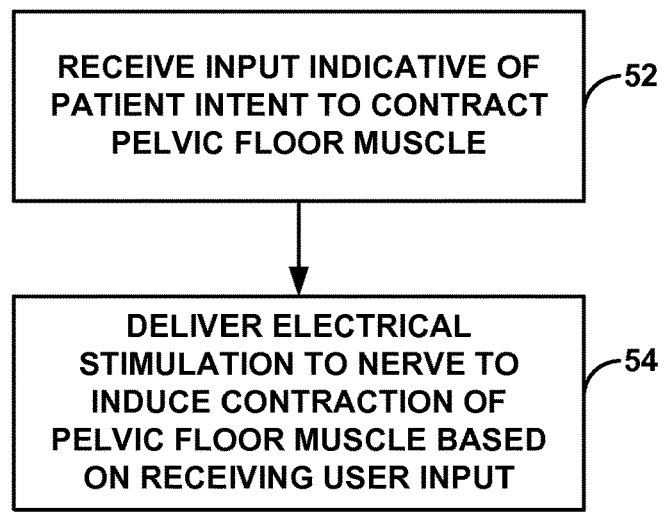
FIG. 4 is a flow diagram illustrating an example technique for delivering electrical stimulation to a patient's sacral nerve or pudendal nerve to strengthen one or more of the patient's pelvic floor muscles.
Figure 5:
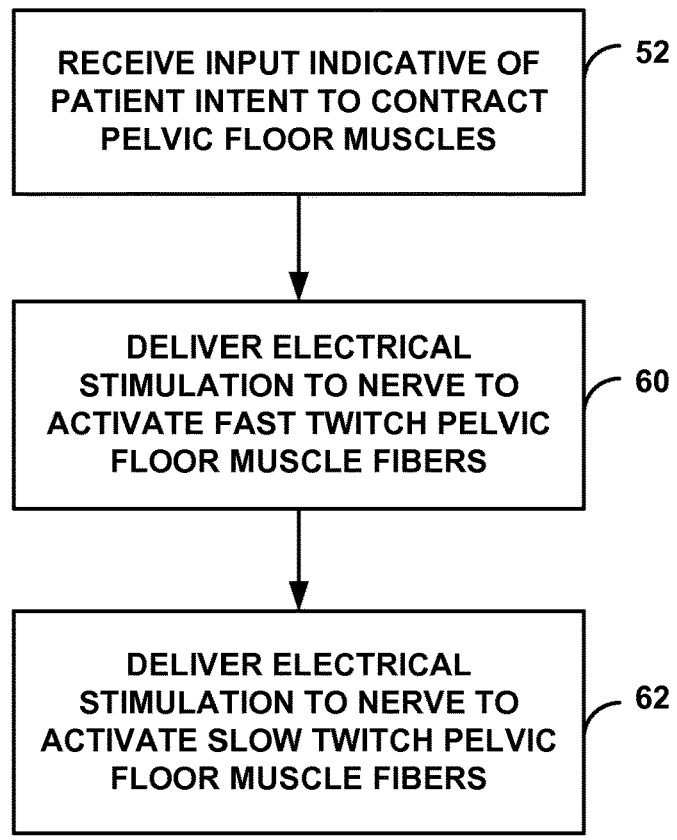
FIG. 5 is a flow diagram illustrating an example technique for delivering electrical stimulation to a patient's sacral nerve or pudendal nerve to activate fast twitch muscle fibers and slow twitch muscle fibers of the patient's pelvic floor muscles.

FIG. 4 is a flow diagram of an example technique that may be performed by IMD 14 for delivering electrical stimulation to patient 12 to strengthen pelvic floor muscles of patient 12. For example, the technique illustrated in FIG. 4 may be used to simulate a Kegel exercise, which can strengthen the pelvic floor muscles of patient 12 in order to treat a pelvic floor disorder of patient 12. While the techniques shown in FIGS. 4 and 5 is described with respect to processor 30 of IMD 14, in other examples, a processor of another device (e.g., one or both programmers 20, 22) can perform some or all of the part of the techniques shown in FIG. 4 and FIG. 5.

According to the technique illustrated in FIG. 4, IMD 14 receives input indicative of intent of patient 12 to contract one or more pelvic floor muscles or an attempt by patient 12 to contract pelvic floor muscles (52). For example, in some examples, patient 12 may provide input to patient programmer 22 indicating that patient 12 is attempting to contract one or more pelvic floor muscles, and patient programmer 22 may transmit an indication to IMD 14 that patient 12 has provided the input, e.g., via telemetry module 46 of patient programmer 22. Telemetry module 34 of IMD 14 may receive the indication. As another example, patient 12 may provide input indicating the intent or attempt to contract the one or more pelvic floor muscles by directly interacting with IMD 14. Patient 12 can, for example, tap the skin superior to IMD 14 in order to impart motion to IMD 14 that is detected by processor 30, e.g., via a signal generated by a motion sensor that is indicative of motion of IMD 14. The pattern, number, duration or other characteristic of the tapping may be associated with a particular patient input, such that processor 30 can receive the indication of patient input based on the detected tapping.

Based on receiving the indication of patient input (e.g., in response to receiving the input), processor 30 controls electrical stimulation module 28 to generate and deliver electrical stimulation to target tissue site 18, which is proximate a sacral nerve, a pudendal nerve, or another nerve of patient 12 that may induce a contraction of one or more pelvic floor muscles (54). As described in further detail below with respect to FIG. 5, the stimulation can be configured to activate slow-twitch muscle fibers, medium-twitch muscle fibers, fast-twitch muscle fibers, or any combination of these muscle fibers.

As discussed previously, the electrical stimulation of the sacral nerve, pudendal nerve, and/or other pelvic floor nerve of patient 12 is configured to induce one or more contractions by the one or more pelvic floor muscles of patient 12. Repetitive contraction over time may help strengthen the pelvic floor muscles of patient 12. Over time, strengthening the pelvic floor muscles of patient 12 in this manner, e.g., via a training schedule or regimen, may allow patient 12 to gain or regain control of the pelvic floor muscles, which may mitigate one or more symptoms associated with the pelvic floor disorder of patient 12. For example, in examples in which patient 12 suffers from a voiding condition, e.g., urinary or fecal incontinence, strengthening the pelvic floor muscles of patient 12 may result in an increased ability of patient 12 to control voiding functions.

Electrical stimulation module 28 of IMD 14 may be configured to deliver electrical stimulation to target tissue site 18 in any suitable manner, e.g., according to any suitable stimulation parameters, schedule, etc., such that the electrical stimulation induces a contraction in the pelvic floor muscles of patient 12 to strengthen the pelvic floor muscles of patient 12. For example, electrical stimulation module 28 can deliver electrical stimulation to target tissue site 18, where the delivered electrical stimulation signal is defined by particular parameter values, e.g., amplitude, frequency, electrode combination, etc., selected to induce a contraction in one or more pelvic floor muscles of patient 12.

In some examples, processor 30 controls electrical stimulation module 28 to generate and deliver electrical stimulation to target tissue site 18 (54) for a predetermined period of time immediately following the receipt of patient input indicative of an attempt by patient 12 to contract one or more pelvic floor muscles or an intent of patient 12 to contract one or more pelvic floor muscles. The predetermined period of time can be, for example, between about 1 minute and about 10 minutes, though it may vary based on various factors, such as the severity of the patient condition or the muscle to which the stimulation is delivered. During the predetermined period of time, the one or more pelvic floor muscles of patient 12 may contract once or may contract a plurality of times. That is, in some examples, the stimulation delivered by electrical stimulation module 28 is configured to induce a one-time momentary contraction of the one or more pelvic floor muscles, while in other examples, the stimulation is configured to induce a plurality of contractions of the one or more pelvic floor muscles over a predetermined period of time, and, in some examples, according to a predetermined pattern. The pattern can be, for example, repetitive contraction of the one or more pelvic floor muscles at regular intervals or at different intervals (e.g., a pseudorandom pattern of muscle contractions).

In some examples, delivering electrical stimulation to induce contraction of pelvic floor muscles within a relatively short period of time, e.g., substantially immediately or within a few seconds, after receiving the input indicative of an intent of patient 12 to contract the pelvic floor muscles or an attempt by patient 12 to contract the pelvic floor muscles may be advantageous in training the pelvic floor muscles. For example, patient 12 may develop new neural pathways that temporally associate the intent or attempt of patient 12 with the actual, induced contraction of the pelvic floor muscles such that, in some examples, over time, patient 12 may regain or improve the ability to contract the pelvic floor muscles autonomously, e.g., without delivery of electrical stimulation.

Additionally, in some examples, electrical stimulation module 28 delivers electrical stimulation to target tissue site 18 according to a training schedule or regimen, which may define a particular time schedule according to which electrical stimulation is delivered, e.g., time duration of on periods and off periods of a stimulation session, number of daily repetitions of one or more stimulation sessions, etc. The training schedule or regimen may be independent of the patient input indicative of the intent to or attempt to contract the one or more pelvic floor muscles, or may be related to the patient input. For example, in some examples, upon receiving the patient input (52), processor 30 of IMD 14 can control electrical stimulation generator 28 to initiate electrical stimulation delivery to target tissue site 18 according to a predetermined training schedule or regimen. As another example, in addition to or instead of initiating therapy delivery upon receiving patient input (52, 54), processor 30 of IMD 14 can control electrical stimulation module 28 to generate and delivery stimulation therapy to patient 12 according to a predetermined training schedule or regimen, where the training schedule or regimen is initiated by processor 30 and/or by patient 12.

FIG. 5 is a flow diagram of an example technique that may be performed by IMD 14 for delivering electrical stimulation to a sacral nerve and/or a pudendal nerve of patient 12 to activate fast twitch and slow twitch pelvic floor muscle fibers of patient 12. As discussed previously, fast twitch and slow twitch pelvic floor muscle fibers may have different functions and, consequently, it may be desirable to activate fast twitch pelvic floor muscle fibers, slow twitch pelvic floor muscle fibers, or a combination of fast twitch and slow twitch pelvic muscle fibers for different applications.

In the example illustrated in FIG. 5, processor 30 of IMD 14 receives input indicative of intent of patient 12 to contract one or more pelvic floor muscles or an attempt by patient 12 to contract one or more pelvic floor muscles (52). As discussed with respect to FIG. 4, in some examples, patient 12 may provide such input via patient programmer 22 or by interacting with IMD 14.

In some examples, a therapy regimen for training the one or more pelvic floor muscles of patient 12 includes activating only slow-twitch muscle fibers of patient 12, only fast-twitch muscle fibers, only medium-twitch muscle fibers of patient 12, or any combination thereof. A clinician of patient 12 may determine, for example, whether strengthening fast twitch, slow twitch, or a combination of fast twitch and slow twitch pelvic floor muscle fibers may be desirable for treating the pelvic floor disorder of patient 12. For example, in some examples, the pelvic floor disorder of patient 12 may be characterized by particular symptoms associated with weakening or degeneration of fast twitch muscle fibers, particular symptoms associated with weakening or degeneration of slow twitch muscle fibers, or particular symptoms associated with weakening or degeneration of both fast twitch muscle fibers and slow twitch muscle fibers. Consequently, the clinician may program IMD 14 to generate and deliver electrical stimulation delivered to patient 12 that is configured to activate the appropriate muscle fibers, whether it be fast-twitch, medium-twitch, slow0twitch, or a combination thereof.

In some examples, the clinician may provide input, e.g., via clinician programmer 20, to establish electrical stimulation parameter values suitable for activating the particular types of pelvic floor muscle fibers that can effectively treat the pelvic floor disorder of patient 12. In other examples, a processor of system 10, e.g. processor 30 or processor 42, may define electrical stimulation that can effectively treat the pelvic floor disorder of patient 12 based on the clinician's input regarding the particular types of pelvic floor muscle fibers that may be responsible for the pelvic floor disorder of patient 12. The stimulation parameters values that are suitable for activating one type of muscle fiber (e.g., fast-twitch, medium-twitch or low-twitch) may differ from those suitable for activating other types of muscle fibers. For example, the electrode combinations, which may change the tissue to which stimulation is delivered, may differ between a stimulation program configured to activate fast-twitch muscle fibers, a stimulation program configured to activate slow-twitch muscle fibers, and a stimulation program configured to activate medium-twitch muscle fibers. In addition to or instead of the electrode combination, the stimulation programs configured to activate the different muscle fibers may have different current or voltage amplitude values, frequencies, or other stimulation parameter values.

In the example illustrated in FIG. 5, patient 12 suffers from a pelvic floor disorder that may be effectively treated by activation of both fast-twitch pelvic floor muscle fibers and slow-twitch pelvic floor muscle fibers. However, in other examples, the pelvic floor disorder of patient 12 may be effectively treated by activating only fast-twitch pelvic floor muscle fibers, only slow-twitch pelvic floor muscle fibers, only medium-twitch muscle fibers, or medium-twitch muscle fibers in combination with one or both of the fast-twitch and slow-twitch muscle fibers.

According to the technique illustrated in FIG. 5, upon receiving input indicating that patient 12 is attempting to or intending on contracting pelvic floor muscles, processor 30 of IMD 14 controls stimulation module 28 to generate and deliver electrical stimulation to target tissue site 18, where the stimulation is configured to activate fast twitch pelvic floor muscle fibers (60). For example, in some examples, IMD 14 may access and implement one or more stimulation programs stored in a memory of system 10, e.g., memory 32 or memory 44, that are designated for activating fast twitch pelvic floor muscle fibers. In some examples, the one or more stimulation programs may specify one or more stimulation parameters, e.g., amplitude, frequency, electrode combination, etc. In addition, in some examples, the one or more stimulation programs may specify a schedule according to which IMD 14 delivers electrical stimulation to patient 12.

According to the technique illustrated in FIG. 5, processor 30 controls stimulation module 28 to generate and deliver electrical stimulation to target tissue site 18 configured to activate slow twitch pelvic floor muscle fibers (Processor 30 may access and implement one or more stimulation programs stored in a memory of system 10, e.g., memory 32 or memory 44, that are designated for activating slow twitch pelvic floor muscle fibers. In some examples, the one or more stimulation programs may specify one or more stimulation parameter s, e.g., amplitude, frequency, electrode combination, etc. In addition, in some examples, the one or more stimulation programs may specify a schedule according to which IMD 14 delivers electrical stimulation to patient 12.

For example, in some examples, electrical stimulation delivery module 28 may generate and deliver stimulation pulses having a relatively high frequency (e.g., between approximately 50 Hz and approximately 70 Hz, such as approximately 66 Hz) to a tissue site proximate a sacral and/or pudendal nerve to activate fast-twitch muscle fibers. In some examples, the stimulation program to activate fast-twitch muscle fibers may be characterized by one or more stimulation sessions, each of which includes an on period of approximately three seconds followed by an off period of approximately 40 seconds in which electrical stimulation is not delivered. As another example, electrical stimulation delivery module 28 may generate and deliver stimulation pulses at a lower relative frequency (e.g., between approximately 10 Hz and approximately 30 Hz) to a tissue site proximate a sacral and/or pudendal nerve to activate slow-twitch muscle fibers. In some examples, the stimulation program to activate slow-twitch muscle fibers may be characterized by one or more stimulation sessions, each of which includes an on period of approximately five seconds, followed by an off period of approximately 40 seconds in which electrical stimulation is not delivered. In some examples, IMD 14 may generate and deliver stimulation configured to activate fast twitch muscle fibers for approximately one minute and may subsequently deliver stimulation configured to activate slow twitch muscle fibers for approximately twenty minutes.

In some examples, a method in accordance with the disclosure may include, with an implantable medical device, delivering electrical stimulation to a nerve of a patient, where the electrical stimulation is configured to activate at least one fast twitch pelvic floor muscle of the patient and at least one slow twitch pelvic floor muscle of the patient to strengthen the pelvic floor muscles. In some examples, a system in accordance with the disclosure may include at least one electrode implanted proximate to a nerve of a patient, an electrical stimulation generator electrically coupled to the at least one electrode, and a processor configured to control the electrical stimulation generator to deliver electrical stimulation via the at least one electrode to the nerve of the patient, where the electrical stimulation is configured to activate at least one fast twitch pelvic floor muscle of the patient and at least one slow twitch pelvic floor muscle of the patient to strengthen the pelvic floor muscles.

The techniques described in this disclosure, including those attributed to IMD 14, clinician programmer 20, and patient programmer 22, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 30 of IMD 14 and/or processor 42 of programmer 22, any one or more parts of the techniques described herein may be implemented by a processor of one of IMD 14, clinician programmer 20, patient programmer 22, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method for training a pelvic floor muscle of a patient with aid of electrical stimulation, the method comprising:
   receiving input, from the patient via an external programmer, indicative of an intent of the patient to contract the pelvic floor muscle of the patient or an attempt by the patient to contract the pelvic floor muscle; and
   controlling an electrical stimulation module to deliver the electrical stimulation to a nerve of the patient according to a predetermined training schedule in response to receiving the input, wherein the electrical stimulation is configured to induce a contraction of the pelvic floor muscle of the patient, and wherein the delivery of the electrical stimulation according to the predetermined training schedule is configured to strengthen the pelvic floor muscle over time such that the patient at least partially regains control over one or more functions controlled by the pelvic floor muscle.

2. The method of claim 1, wherein the electrical stimulation comprises a frequency of 20 Hertz to 50 Hertz.

3. The method of claim 1, wherein receiving input comprises receiving input from the patient via a user interface of the external programmer.

4. The method of claim 1, further comprising:
   receiving input indicative of tapping of an implantable medical device, wherein the receipt of the signal indicative of the tapping comprises another input indicative of the intent of the patient to contract the pelvic floor muscle of the patient or the attempt by the patient to contract the pelvic floor muscle; and
   controlling the electrical stimulation module to deliver the electrical stimulation to the nerve of the patient according to the predetermined training schedule in response to receiving the another input.

5. The method of claim 1, wherein controlling the electrical stimulation module to deliver electrical stimulation according to the predetermined training schedule comprises controlling the electrical stimulation module to deliver electrical stimulation to the patient during at least one stimulation session, wherein the at least one stimulation session comprises a plurality of cycles of electrical stimulation.

6. The method of claim 5, wherein the plurality of cycles of electrical stimulation comprises ten cycles of electrical stimulation and wherein controlling the electrical stimulation module to deliver electrical stimulation during the at least one stimulation session comprises controlling the electrical stimulation module to deliver the electrical stimulation during three separate stimulation sessions within a twenty four hour period.

7. The method of claim 5, wherein a time duration of the at least one stimulation session is twenty minutes and wherein controlling the electrical stimulation module to deliver electrical stimulation during the at least one stimulation session comprises controlling the electrical stimulation module to deliver the electrical stimulation during two separate stimulation sessions within a twenty four hour period.

8. The method of claim 5, wherein each cycle of the plurality of cycles comprises an on period in which electrical stimulation is delivered to the patient and an off period in which electrical stimulation is not delivered to the patient, wherein a time duration of the on period is ten seconds and a time duration of the off period is 20 seconds, and wherein the electrical stimulation is characterized by a frequency of 20 Hertz to 50 Hertz.

9. The method of claim 5, wherein each cycle of the plurality of cycles comprises an on period in which electrical stimulation is delivered to the patient and an off period in which electrical stimulation is not delivered to the patient, wherein a time duration of the on period is 3 seconds and a time duration of the off period is 40 seconds, and wherein the electrical stimulation is characterized by a frequency of 50 Hertz to 70 Hertz.

10. The method of claim 5, wherein each cycle of the plurality of cycles comprises an on period in which electrical stimulation is delivered to the patient and an off period in which electrical stimulation is not delivered to the patient, wherein a time duration of the on period is 5 seconds and a time duration of the off period is 40 seconds, and wherein the electrical stimulation is characterized by a frequency of 10 Hertz to 30 Hertz.

11. The method of claim 1, wherein the nerve comprises at least one of a sacral nerve, at least one branch of the sacral nerve, a pudendal nerve, or at least one branch of the pudendal nerve.

12. The method of claim 1, wherein the electrical stimulation is configured to activate at least one of slow twitch muscle fibers, medium twitch muscle fibers, or fast twitch muscle fibers of the pelvic floor muscle.

13. The method of claim 1, wherein controlling the electrical stimulation module to deliver electrical stimulation to a nerve of the patient according to the predetermined training schedule in response to the input comprises controlling the electrical stimulation module to deliver electrical stimulation to the nerve of the patient within two seconds after receiving the input.

14. A system for training a pelvic floor muscle of a patient with aid of electrical stimulation, the system comprising:
at least one electrode configured for implantation proximate to a nerve of the patient;
an electrical stimulation module electrically coupled to the at least one electrode and configured to generate and deliver the electrical stimulation; and
a processor configured to receive input, from the patient via an external programmer, indicative of an intent of the patient to contract the pelvic floor muscle of the patient or an attempt by the patient to contract the pelvic floor muscle, and to control the electrical stimulation module to deliver electrical stimulation via the at least one electrode to the nerve of the patient and according to a predetermined training schedule in response to receiving the input, wherein the electrical stimulation is configured to induce a contraction in the pelvic floor muscle of the patient, and wherein the delivery of the electrical stimulation by the electrical stimulation module according to the predetermined training schedule is configured to strengthen the pelvic floor muscle of the patient over time such that the patient at least partially regains control over one or more functions controlled by the pelvic floor muscle.

15. The system of claim 14, wherein the processor is configured to control the electrical stimulation module to deliver electrical stimulation according to the predetermined training schedule at a frequency of 20 Hertz to 50 Hertz in response to receiving the input.

16. The system of claim 14, further comprising the external programmer comprising a user interface, wherein the processor is configured to receive the input from the patient via the user interface.

17. The system of claim 14, further comprising:
an implantable medical device; and
a motion sensor integral with the implantable medical device, wherein the motion sensor is configured to generate a signal indicative of tapping of the implantable medical device, and wherein the processor is configured to receive the signal indicative of tapping as another input indicative of the intent of the patient to contract the pelvic floor muscle of the patient or the attempt by the patient to contract the pelvic floor muscle, and wherein the processor is configured to control the electrical stimulation module to deliver the electrical stimulation via the at least one electrode to the nerve of the patient and according to the predetermined training schedule in response to receiving the another input.

18. The system of claim 14, wherein the processor is configured to control the electrical stimulation module to deliver electrical stimulation to the patient according to the predetermined training schedule during at least one stimulation session, wherein the at least one stimulation session comprises a plurality of cycles of electrical stimulation.

19. The system of claim 18, wherein the plurality of cycles of electrical stimulation comprises ten cycles of electrical stimulation and wherein delivering electrical stimulation during at least one stimulation session comprises delivering the electrical stimulation during at least three separate stimulation sessions within a twenty four hour period.

20. The system of claim 18, wherein a time duration of the at least one stimulation session is twenty minutes and wherein delivering electrical stimulation during at least one stimulation session comprises delivering the electrical stimulation during at least two separate stimulation sessions within a twenty four hour period.

21. The system of claim 18, wherein each cycle of the plurality of cycles comprises an on period in which electrical stimulation is delivered to the patient and an off period in which electrical stimulation is not delivered to the patient, wherein a time duration of the on period is ten seconds and a time duration of the off period is 20 seconds, and wherein the electrical stimulation is characterized by a frequency of 20 Hertz to 50 Hertz.

22. The system of claim 18, wherein each cycle of the plurality of cycles comprises an on period in which electrical stimulation is delivered to the patient and an off period in which electrical stimulation is not delivered to the patient, wherein a time duration of the on period is 3 seconds and a time duration of the off period is 40 seconds, and wherein the electrical stimulation is characterized by a frequency of 50 Hertz to 70 Hertz.

23. The system of claim 18, wherein each cycle of the plurality of cycles comprises an on period in which electrical stimulation is delivered to the patient and an off period in which electrical stimulation is not delivered to the patient, wherein a time duration of the on period is 5 seconds and a time duration of the off period is 40 seconds, and wherein the electrical stimulation is characterized by a frequency of 10 Hertz to 30 Hertz.

24. The system of claim 14, wherein the nerve comprises at least one of a sacral nerve, at least one branch of the sacral nerve, a pudendal nerve, or at least one branch of the pudendal nerve.

25. The system of claim 14, wherein the processor is configured to control the electrical stimulation module to deliver electrical stimulation via the at least one electrode to the nerve of the patient according to the predetermined training schedule within two seconds after receiving the input.

26. The system of claim 14, wherein the electrical stimulation delivered by the electrical stimulation module to induce the contraction in the pelvic floor muscle of the patient comprises delivery of a first electrical stimulation followed by delivery of a second electrical stimulation, wherein the first electrical stimulation is configured to activate fast-twitch pelvic floor muscle fibers and the second electrical stimulation is configured to activate slow-twitch pelvic floor muscle fibers.

27. The system of claim 26, where the first electrical stimulation has a first frequency and the second electrical stimulation has a second frequency less than the first frequency.

28. The system of claim 26, where the first electrical stimulation has a first frequency of approximately 50 Hertz to approximately 70 Hertz, and the second electrical stimulation has a second frequency of approximately 10 Hertz to approximately 30 Hertz.

29. The system of claim 14, wherein the processor is configured to control the delivery of the electrical stimulation by the electrical stimulation module such that the induced contraction of the pelvic floor muscle is substantially simultaneous with the patient intent to contract the pelvic floor muscle or the patient attempt to contract the pelvic floor muscle.

30. A system for training a pelvic floor muscle of a patient with aid of electrical stimulation, the system comprising:
means for receiving input, from the patient via an external programmer, indicative of an intent of the patient to contract the pelvic floor muscle of the patient or an attempt by the patient to contract the pelvic floor muscle; and means for delivering the electrical stimulation to a nerve of the patient according to a predetermined training schedule in response to receiving the user input, wherein the electrical stimulation is configured to induce a contraction of the pelvic floor muscle of the patient and delivery of the electrical stimulation according to the predetermined training schedule is configured to strengthen the pelvic floor muscle over time such that the patient at least partially regains control over one or more functions controlled by the pelvic floor muscle.

31. The system of claim 30, wherein the means for delivering electrical stimulation according to the predetermined training schedule is configured to deliver electrical stimulation at a frequency of 20 Hertz to 50 Hertz in response to receiving the input.

32. A system for training a pelvic floor muscle of a patient with aid of electrical stimulation, the system comprising:
   at least one electrode configured for implantation proximate to a nerve of the patient;
   an electrical stimulation module electrically coupled to the at least one electrode and configured to generate and deliver the electrical stimulation;
   an implantable medical device;
   a motion sensor integral with the implantable medical device, wherein the motion sensor is configured to generate a signal indicative of tapping of the implantable medical device; and
   a processor configured to receive the signal indicative of the tapping as input indicative of an intent of the patient to contract the pelvic floor muscle of the patient or an attempt by the patient to contract the pelvic floor muscle, and to control the electrical stimulation module to deliver electrical stimulation via the at least one electrode to the nerve of the patient and according to a predetermined training schedule in response to receiving the input, wherein the electrical stimulation is configured to induce a contraction in the pelvic floor muscle of the patient, and wherein the delivery of the electrical stimulation by the electrical stimulation module according to the predetermined training schedule is configured to strengthen the pelvic floor muscle of the patient over time such that the patient at least partially regains control over one or more functions controlled by the pelvic floor muscle.

* * * * *